(12) United States Patent
Lanzara

(10) Patent No.: US 6,593,094 B2
(45) Date of Patent: *Jul. 15, 2003

(54) COMPOSITIONS TO ENHANCE THE EFFICACY AND SAFETY OF BIO-PHARMACEUTICAL DRUGS

(76) Inventor: Richard G. Lanzara, 30 W. 86th St. Apartment 1B, New York, NY (US) 10024

( * ) Notice: Subject to any disclaimer, the term of this patent is extended or adjusted under 35 U.S.C. 154(b) by 62 days.

This patent is subject to a terminal disclaimer.

(21) Appl. No.: 09/783,115

(22) Filed: Feb. 14, 2001

(65) Prior Publication Data

US 2001/0004529 A1 Jun. 21, 2001

Related U.S. Application Data

(63) Continuation-in-part of application No. 08/764,145, filed on Dec. 12, 1996, which is a continuation-in-part of application No. 08/407,911, filed on Mar. 21, 1995, now Pat. No. 5,597,699, which is a continuation-in-part of application No. 08/188,951, filed on Jan. 31, 1994, now abandoned, which is a continuation-in-part of application No. 07/954,865, filed on Sep. 30, 1992, now abandoned.

(51) Int. Cl.[7] ............... G01N 33/567; A61K 31/535; A61K 31/135
(52) U.S. Cl. ............... 435/7.21; 514/236.2; 514/652
(58) Field of Search ............... 435/7.21; 514/236.2, 514/652

(56) References Cited

U.S. PATENT DOCUMENTS 5,597,699 A    1/1997   Lanzara

OTHER PUBLICATIONS

Fernandes, et al. "B–Adrenoceptor Desensitization in Guinea Pig. etc."; Euro. J. of Pharm.; 159:135–145; 1988.
Dilger, et al.; "Direct Measurement . . . Channel"; Biophys. J. Biophys. Soc.; vol. 57 (Apr.): 723–731 (1990).
Geoffroy et al. "Reduction of Desensitization . . . by Antagonists"; Molecular Pharmacology 39: 587–591, 1991.
Stephenson; "A Modification of Receptor Theory." Brit. J. of Pharmacology; vol. 11: 379–393; 1956.
Keen; Testing Models of Agonism for G–Protein–Coupled Receptors; TIPS; v.12: 371–74.
Colquhoun, D.; "Validity of the Operational Model"; Trends in Pharm. Sci. (TIPS) V. 10:17; 1989.
White, D.C. et al.; "Preservation of Myocardial B . . . Heart Failure After Myocardial Infarction"; PNAS 97; pp. 5428–5433; 2000.
del Castillo and Katz; "Interaction at End–plate . . . Choline Derivatives"; Proc.Roy.Sci.Lond.; 146:369–381 (1957).
Xin Fu et al.; "Antiphylactic Effects . . . Myometrial Contractile Activity In Vitro"; Obstetrics & Gynecology; vol. 82: 532–38; 1993.
Otto–Erich Brödde; "Beta 1 and Beta 2 Adrenoceptors in the Human Heart: Properties . . . Heart Failure"; Pharmacological Review; vol. 43, No. 2, pp. 203–242.
Lanzara, R.G.; "A Novel Biophysical Model for Receptor Activation"; Pres. to XII Intern. Congress of Phar., Montréal, Québec, Canada, Jul. 1994.
Lanzara, R.G.; "Weber's Law Modeled . . . Balance"; Mathematical Biosciences; vol. 122: 89–94; 1994.
Rocha y Silva; "Influence of pH . . . Guinea Pig Ileum" Arch. Int. Pharmacodyn.; CXXVII, No. 3–4, 355–74, '60.
Davies, A.O.; "Rapid Desensitization . . . Acidosis"; J. of Clin. Endocrin. a. Metabol.; vol. 59: 398–405; 1984.
Hall, M.D. et al.; "Differentiation . . . Modifying Agents"; Neurochem. Research; vol. 11, No. 6, 891–912; 1986.
Asselin, J. et al.; "Effect of pH . . . Agonists a. Antagonists . . . Receptors"; Biochem. J.; 216: 11–19; 1983 (Bel.).
Barlow, R.B. et al.; "Effects of pH . . . Raf Diaphragm . . . "; Brit. J. of Pharmacol.; 18: 543–549; 1962.
Katz, B. et al.; "A Study . . . 'Desensitization'. . . End–plate"; J. Phisiol.; 138: 63–80; 1957.
Cachelin, A.B. and Colquhoun, D.; "Desensitization . . . Frog End–plates . . . Voltage Clamp"; J. of Physiology; vol. 415: 159–188; 1989.
Gende, O.A. et al.; "Effecto de las Variaciones del pH . . . Beta Adrenergico"; Acta. Physiol. Pharmacol. Latinoam. vol. 35: 205–216, 1985 (Span.) Abstract in English.

Primary Examiner—Donna Wortman
(74) Attorney, Agent, or Firm—Fredric Morelle

(57) ABSTRACT

Optimal ratios of pharmaceutical compositions of β-1 and β-2 agonists with their respective antagonists. Safer, more cost-effective drugs for heart and lung therapies are made by combining specific antagonists with their agonists to prevent desensitization of cellular receptors, reducing some of the unwanted side-effects of the agonist drugs alone. Determining the optimal concentration of an antagonist or inhibitor, which is necessary to prevent desensitization, without causing unnecessary and unwanted inhibition, creates a new class of pharmaceuticals. To derive an optimum ratio for a specific composition, a formulative method is provided to detail how competitive antagonists of the receptor should be combined with agonists, in specific proportions, to maximize and maintain receptor response throughout drug administration. The "optimal ratio" methodology used to determine a specific agonist/antagonist composition, to prevent β-1 or β-2 receptor desensitization, is experimentally verified and validated for specific compositions. Alteration of a specific ratio is practiced to account for the pharmacokinetic/dynamic differences between animals and humans and within human populations.

16 Claims, 8 Drawing Sheets

COMPOSITIONS TO ENHANCE THE EFFICACY AND SAFETY OF BIO-PHARMACEUTICAL DRUGS

REFERENCES TO RELATED APPLICATIONS

This application is a Continuation-in-Part (CIP) of U.S. Ser. No. 08/764,145, filed on Dec. 12, 1996, which is a CIP of U.S. Ser. No. 08/407,911, filed on Mar. 21, 1995 and issued as U.S. Pat. No. 5,597,699, which was a CIP of U.S. Ser. No. 08/188,951, filed on Jan. 31, 1994, abandoned, which was a CIP of U.S. Ser. No. 07/954,865, filed on Sep. 30, 1992, abandoned.

STATEMENT REGARDING FEDERALLY SPONSORED RESEARCH OR DEVELOPMENT

Not Applicable

BACKGROUND OF THE INVENTION

1. Field of the Invention

This invention relates generally to drug compositions that optimize or maximize the therapeutic effects of particular receptor-specific agonists, while concurrently preventing or, in the least, significantly ameliorating receptor desensitization, and which derive from the methodology of the inventor's U.S. Pat. No. 5,597,699. More particularly, the instant invention sets forth the methodological improvements, and compositions, that are derived from application of that patent's teachings. These improvements usher in classes of compositions that are pharmaceutically compensated (or fitted) to harmonize with physiologies of diverse therapy recipients.

2. Discussion of Relevant Art

An agonist is a substance/drug that has affinity for and stimulates physiologic activity at cell receptors that are normally stimulated by naturally occurring substances. As used throughout, an agonist is such a substance/drug that produces a maximal or a nearly maximal response, whereas an antagonist or inhibitor is a substance or molecule that produces no response, but can block the action of the drug-agonist. A partial agonist produces a moderate response and can also block the response of the receptor to the agonist-compound. A competitive antagonist is a substance that competes with the agonist for the receptor, but produces no response. [Note: Hereinafter, the combination of a specific agonist with a suitable antagonist or inhibitor will have one of the identifying forms of notation: agonist-antagonist or agonist/antagonist or antagonist: agonist; in such instances, the dash (-), slash (/) and semicolon (:) connoting the same.]

More than twenty years ago, the idea that beta-adrenergic antagonists could be used to treat heart failure was considered heretical although clinical data were emerging to support this viewpoint (White, D. C., Hata, J. A., Shah, A. S., Glower, D. D., Lefkowitz, R. J., and Koch, W. J., "Preservation of myocardial β-adrenergic receptor signaling delays the development of heart failure after myocardial infarction." *PNAS*, 97: 5428–5433 (2000) and references therein). Previously it was thought that failing hearts required positive inotropic support and that the use of beta-antagonists would depress heart function. After more than two decades, the conventional wisdom on this point has been overturned.

In heart failure, there is a biochemical alteration of the β-adrenergic receptor signaling system leading to the loss of cardiac inotropic reserve through β-adrenergic receptor desensitzation. It was demonstrated in a recent study (White, D. C., et al.) that observed desensitization and down-regulation of β-adrenergic receptors, seen in the failing heart, is deleterious for normal heart function (see 2 and references therein). In this study, paraphrasing what the authors wrote:

(1) In a rabbit model of heart failure induced by myocardial infarction, which recapitulates the biochemical β-adrenergic receptor abnormalities seen in human heart failure, delivery of the β-adrenergic receptor kinase ct transgene at the time of myocardial infarction prevents the rise in β-adrenergic receptor kinase 1 activity and expression and thereby maintains β-adrenergic receptor density and signaling at normal levels. Rather than leading to deleterious effects, cardiac function is improved, and the development of heart failure is delayed. These results appear to challenge the notion that dampening of β-adrenergic receptor signaling in the failing heart is protective, and they may lead to novel therapeutic strategies to treat heart disease via inhibition of β-adrenergic receptor kinase 1 and preservation of myocardial β-adrenergic receptor function.

(2) The most promising current therapies in heart failure is the use of β-adrenergic receptor antagonists, which presumably block the chronic activation of the β-adrenergic receptor system by norepinephrine. β-adrenergic receptor kinase 1 up-regulation could be the "first-response" feedback mechanism responding to the enhanced sympathetic nervous system activity because the expression of β-adrenergic receptor kinase 1 in the heart can be stimulated by catecholamine exposure. An opposing hypothesis, however, is that the increase in myocardial G protein-coupled receptor kinase (GRK) activity often observed in the failing heart can mediate changes within the β-adrenergic receptor system that are not protective but that rather take part in the pathogenesis of heart failure. If such is the case, then the inhibition of β-adrenergic receptor kinase 1 might represent a novel therapeutic target in the treatment of the failing heart.

(3) To address specifically the issue of whether β-adrenergic receptor desensitization might have maladaptive rather than adaptive consequences in the setting of heart failure, we have delivered a peptide inhibitor of β-adrenergic receptor kinase 1 activity via in vivo intracoronary adenoviral-mediated gene delivery to the hearts of rabbits that have a surgically induced myocardial infarction (MI). We have shown previously that this model of MI in rabbits results in overt heart failure within 3 weeks, including pleural effusions, ascites, and significant hemodynamic dysfunction.

(4) The conventional view of the role of sympathetic activation in heart failure is that the resultant elevated myocardial β-adrenergic receptor kinase 1 levels and β-adrenergic receptor desensitization in the dysfunctional heart are actually protective mechanisms. Abrogation of such compensatory mechanisms, it has been reasoned, would only worsen the physiologic deterioration caused by excess catecholamine stimulation. Indeed, the chronic use of β-agonists in heart failure is harmful.

(5) First, administration of an oral β-agonist leads to further β-adrenergic receptor down-regulation in the lymphocytes of patients with heart failure. Additionally, the β-adrenergic receptor kinase 1 expression is increased after β-adrenergic receptor stimulation. Therefore, the use of β-agonists in heart failure patients exacerbates disturbances in the myocardial β-adrenergic receptor system, leading to further receptor down-regulation and increases in β-adrenergic receptor kinase 1. In contrast, restoration of β-adrenergic receptor signaling through gene delivery of the β-adrenergic receptor kinase ct has a fundamentally opposite effect at a molecular level, i.e., it preserves the number of β-adrenergic receptors and inhibits β-adrenergic receptor kinase 1. [end paraphrasing]

It is interesting that β-adrenergic receptor kinase 1 inhibition shares with β-blockade the potential to normalize or remodel signaling through the cardiac β-adrenergic receptor system in heart failure. Moreover, both treatments lower cardiac GRK activity, enhance catecholamine sensitivity, and raise or preserve myocardial levels of β-adrenergic receptors (White, et al. and included references). Thus, it is possible that part of the salutary effects of β-blockers on the failing heart is because of their demonstrated ability to reduce expression of β-adrenergic receptor kinase 1 in the heart. With the overwhelming positive data showing the beneficial effects of β-blockers in the treatment of heart failure, it is reasonable to question whether the strategy of adding a β-adrenergic receptor kinase 1 inhibitor adds anything novel to the therapeutic armamentarium. However, given the results of this study, it is apparent that β-antagonist therapy and β-adrenergic receptor kinase 1 inhibition may in fact be complementary therapeutic modalities. [See SUMMARY OF THE INVENTION]

Present theories of receptor activation calculate the response of a receptor as some function of an agonist-receptor complex. There have been several modifications and criticisms of receptor theory (see, for example Keen, M.; Testing Models of agonist for G-Protein Coupled Receptors: *Trends Pharmacol. Sci.* 12, 371–374, 1991), but none of these treatments examined the discrete change induced by ligand binding to two equilibrium states of a receptor and, consequently, no one has developed the instant (and exacting) method for determining actual drug compositions based upon an optimal ratio of agonist to antagonist which effectively prevent desensitization of cellular receptors that are normally and incipiently responsive to a host of agonists. Careful experimental investigations of several different receptor systems have revealed that receptor theory fails to describe the observed responses in a number of cases. Also, the phenomenon of rapid desensitization has been difficult to model by modem receptor theories. Originally many of these experimental observations were reported in 1957 by del Castillo and Katz in their pioneering work on desensitization (del Castillo, J. and Katz, B. *Proc. Roy. Soc. Lond.* 146, 369–381, 1957). The present theories are inadequate for at least two fundamental reasons; first, they fail to describe relevant experimental observations, except for limited cases and second, they offer only a "black box" description instead of a physicochemical explanation for receptor response.

In 1991, Geoffrey et al. found that competitive antagonists of a glutamate receptor decreased the desensitization of the receptor (See Geoffrey, M., et al. *Molecular Pharmacology* 39, 587–591; 1991). They concluded, in this study, that such paradoxical behavior could not be described by the current theories of pharmacologic action deriving from (for example) experimental observations first recorded in 1957 by del Castillo & Katz performing their pioneering work on desensitization. Until most recently, no theory has been able to adequately explain how the behavior observed by Geoffrey et al. occurs; and, the utility of mixing competitive antagonists (or partial agonists) with agonists accurately and, therefore, efficiently to prevent receptor desensitization has been all but overlooked.

Other articles that show the utility (in vivo) of using antagonist/agonist compositions, to prevent receptor desensitization, are extant. One such article is "Antitacyphylactic Effects of Progesterone and Oxytocin on Term Human Myometrial Contractile Activity In Vitro" by Xin Fu, MD, Masoumeh Rezapour, MD, Mats Löfgren, MD, PhD, Ulf ulmsten, MD, PhD, and Torbjörn Bäckström, MD, PhD, all of the Department of Gynecology and Obstetrics, University Hospital, Uppsala, Sweden and published in *Obstetrics & Gynecology* (1993; 82: 532–8). Therein, Xin Fu et al. conclude that a quantum of an antagonist, progesterone, is observed to reverse the tachyphylaxis (desensitization) to oxytocin (agonist) of human myometrium. A method for quantifying the compounds for this phenomenon is not suggested, particularly for arriving at proper dosages of the antagonist, for consistently achieving the reversal. Nor for that matter, do Xin Fu et al. provide formulas that will maintain a maximal receptor response.

Another disclosure is of certain importance in the quest for in vivo studies to support modeling investigational techniques in drug research: "Beta1 and Beta2 Adrenoceptors in the Human Heart: Properties, Function, and Alterations in Chronic Heart Failure" by Otto-Erich Brodde of Bio-chemisches Forschungslabor, Medizinische Klinik and Poliklinik, Abteilung für Nieren-und Hochdruckkrankheiten, Universitätsklinikum, Essen, Germany. (*Pharmacological Review,* 1991, Vol. 43, No. 2). This is a detailed study on chronic heart failure which discusses a recognized utility of using Beta-AR (beta-adrenergic receptor) antagonists for patients in certain types of heart failure (pp. 228–230) and which hypothesizes that such work by occupying Beta-ARs and prevent desensitization of cardiac Beta-ARs (see p.233 and references therein). [NOTE: No further information is detailed which would inform one of ordinary skill how to quantify the portions of antagonists necessary to fully retard i.e., prevent "downregulation" (desensitization, ibid p. 233) of Beta-ARs.]

As recently as Jul. 24, 1994, the instant inventor presented his work "A Novel Biophysical Model for Receptor Activation" (R. Lanzara, CUNY, New York and Bio-Balance, Inc., New York, N.Y.) to the XIIth International Congress of Pharmacology at Montréal, Québec, Canada Also presented was a paper published by him concerning Weber's Law ("Weber's Law Modeled by the Mathematical Description of a Beam Balance", *Mathematical Biosciences,* 122:89–94 (1994)). These works are included for their teachings on the instant concept, methods of calculation to provide quanta of antagonist: agonist necessary for achieving the objectives of the invention and demonstrate objectively by use of in vivo empirical studies that the invention is a substantial improvement to the prior art and a significant advancement in the field.

INCORPORATION BY REFERENCE

The following of the aforementioned works: Geoffroy et al. "Reduction of Desensitization of a Glutamate Ionotropic Receptor by Antagonists" *Molecular Pharmacology* 39: 587–91 (1991); Xin Fu et al., "Antitachyphylactic Effects of Progesterone and Oxytocin on Term Human Myometrial Contractile Activity In Vitro", *Obstetrics & Gynecology,* 82: 532–38 (1993); OttoErich Brodde, "Beta1 and Beta2 Adrenoceptors in the Human Heart: Properties, Function, and Alterations in Chronic Heart Failure", *Pharmocological Review,* Vol. 43, No. 2 (1991); Lanzara, R. "A Novel Bio-physical Model for Receptor Activation" Dept. of Allied Health Sci., CUNY, NY, N.Y. and Bio-Balance Inc., NY, N.Y.; and, Lanzara, R. "Weber's Law Modeled by the Mathematical Description of a Beam Balance", *Mathematical Biosciences,* 122: 89–94 (1994) are incorporated herein by reference.

SUMMARY OF THE INVENTION

The problem is solved for determining the optimal ratio for the concentration of an antagonist- or inhibitor-to-agonist which is sufficient to prevent cellular receptor desensitization, and, without causing unnecessary and unwanted inhibition, maintaining a maximal response. The instant, improved method and formulas describe not only f, the concentration of the antagonist relative to that of the agonist (given by $K_i$, the dissociation constant of the antagonist, divided by $\phi$, the square root of one-half of the product of the two dissociation constants of the drug-agonist for the receptor), but provide a methodology for obtaining the various formulary factors by which I derive the specific ratios of the selected agonist and antagonist for receptor classes among the diverse animal species. When higher ratios of the antagonist are used, more inhibition of the response occurs; and when lower ratios are used, desensitization results.

It is noted that, in the relevant art, there exists a method for calculating drug efficacy by utilization of easily identifiable biophysical parameters. Additional to both in vitro and in vivo data gleaned from the incorporated references (Xin Fu, et al. and Otto-Erich Brodde, ibid.), I initially had performed an in vitro test on Guinea pig trachea, a widely used substitute tissue for pharmacologic research on human trachea, to determine the optimal composition of an antagonist (propranolol) which is mixed with an agonist (isoproterenol) in order to prevent receptor desensitization produced by a large concentration of said agonist (isoproterenol=25 $\mu$M). Specifically, the experimental data and the calculated values were compared. The agreement of the experimental data with the calculated value for $f=K_i/\phi$ was within one and one-quarter percent (1.25%; calculated=0.0395 vs. experimental=0.04). This excellent result validated the method for calculating the optimal ratio of the agonist/antagonist compositions to prevent receptor desensitization. This was a specific test of this invention to determine the optimal ratio of propranolol to isoproterenol in the Guinea pig trachea and proved that there exists a maximally effective ratio that finds utility in its ability to prevent agonist-induced drug desensitization.

The instant method of preventing β-adrenergic receptor desensitization or down-regulation, by creating the optimal ratio of agonist to antagonist combinations, is a complementary therapeutic strategy to what the recent study (White, D. C. et al., ibid.) suggests as an appropriate therapy to maintain β-adrenergic receptor signaling in patients with heart failure. The difference between our approaches is that while the authors of this study advocate the delivery of an intracellular inhibitor of the β-adrenergic receptor kinase through the "β-adrenergic receptor kinase ct transgene", I advocate that, by the proper titration of agonist to antagonist, the same beneficial effects will occur. Many of these effects were mentioned by these authors as resulting from both β-blockade therapy and their own "transgene therapy". The instant teaching is that, because the endogenous levels of catecholamines are usually elevated in patients with heart failure, concomitant use of β-blockers reduces the desensitization of these receptors in these patients with higher than normal norepinephrine or epinephrine levels. This can be more easily understood by observing that in FIG. 2 of my 1997 patent (Lanzara '699, ibid.), the use of any inhibitors (β-blockers) will improve the relative response for the desensitized portion of the curve (to the right of the peak). Therefore, the Lanzara compositions represent the best mode of practice to maintain the β-adrenergic signaling in the failing myocardium.

Having been encouraged by initial successes, I have been able to compound a host of pharmaceuticals that are the scientifically derived optimal ratios, i.e., agonist-antagonist, that work best for the largest population, yet have the least side-effect impact. More to the latter characteristic, I have found, through further empirical studies that, relative to heart therapies, the invention's new compositions presented with significantly less arrhythmias than did agonists alone. A specific composition comprising isoproterenol with metoprolol in the ratio of 1:85, Iso:Met, comprising for a single microgram amount of isoproterenol HCl, 85 micrograms of metoprolol tartrate, is used as a safer and more efficacious alternative to isoproterenol alone. I alter this ratio in a manner normally practiced in the pharmaceutical industry to account for the pharmacokinetic and pharmacodynamic differences between animals and humans and within populations.

DETAILED DESCRIPTION OF THE PREFERRED EMBODIMENT

For all of the known receptors, most experimental observations have shown that agonist ligands display two-site binding while antagonist ligands display one-site binding. The experimental observations can be understood as a preferential binding of the agonists for one form of the receptor. This gives rise to the observed two-site binding and the two dissociation constants of the drug for the receptor. This is demonstrated to be a direct consequence of the efficacy of the agonist and is a measure of the response of the system. By this reasoning, antagonists would display equal or nearly equal affinities for each form of the receptor. This is observed as one-site binding and a single dissociation constant for antagonist binding to receptors. For a receptor that exists in two states, an ionizable receptor was selected as a likely example because there is experimental evidence to support this. (See: Davies, A. O. *J. Clinical Endocrinology & Metabolism* 59, 398–405 (1984); Gende, O. A., Hurtado, M. C. C. & Cingolani, H. E. *Acta Physiol. Pharmacol. Latinoam.* 35, 205–216 (1985); Hall, M. D., et al. *Neurochemical Research* 11, 891–912 (1986); Asselin, J., et al. *Biochem. J.* 216, 11–19 (1983); Barlow, R. B. & Hamilton, J. T. *Brit. J. Pharmacol* 18, 543–549 (1962); Battaglia, G., Shannon, M., Borgundvaag, B. and Titeler, M. *Life Sciences* 33, 2011–2016 (1983); and Rocha E. Silva, M. *Arch. Int. Pharmacodyn.* 128, 355–374 (1960)).

Figure 1:
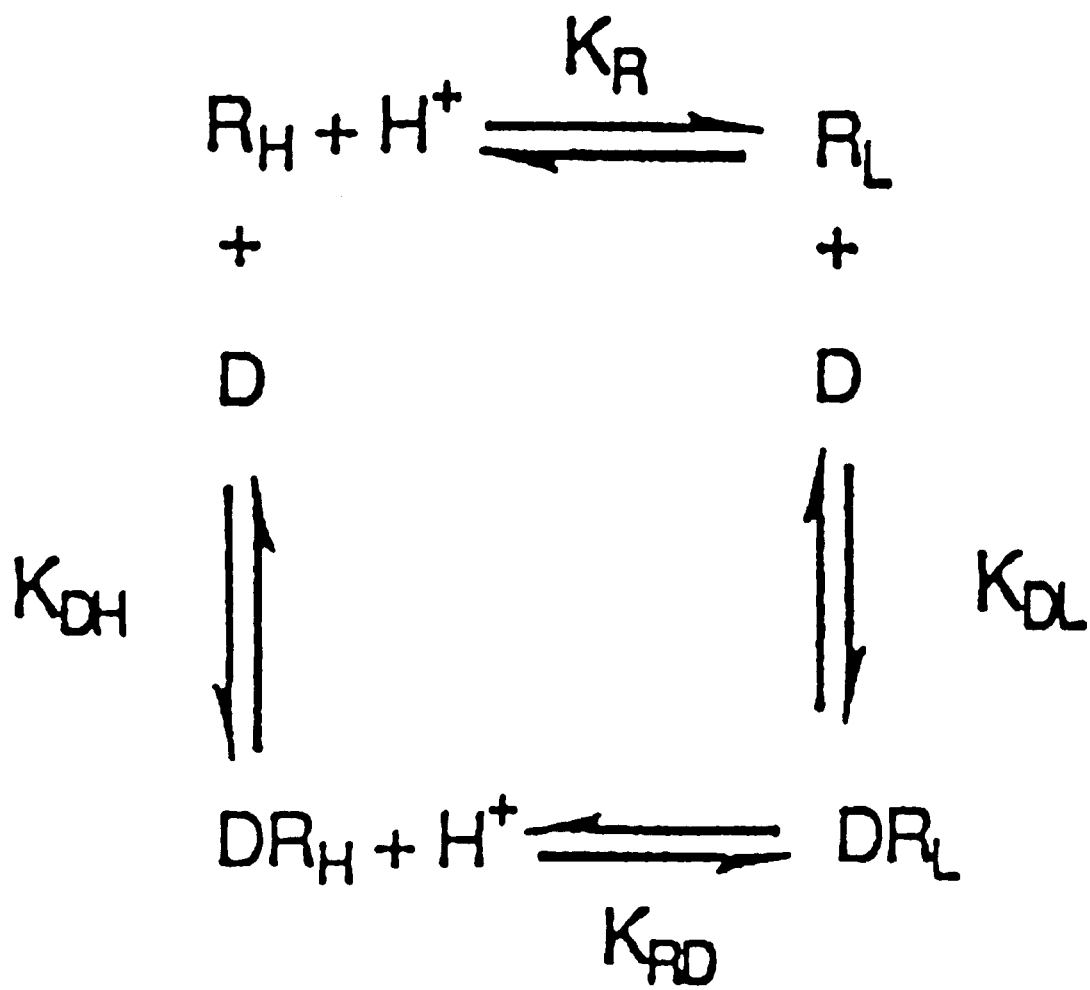
FIG. 1 depicts ligand equilibria with the ionic forms of the receptor.

In FIG. 1, the equilibria of the ligand with the ionic forms of the receptor are shown. The two free forms of the receptor ($R_H$ and $R_L$) which can exist in either an ionized ($R_H$) form or a non-ionized ($R_L$) form, respectively, react with the drug D, with two different dissociation constants, $K_{DH}$ and $K_{DL}$; $DR_H$ and $DR_L$ are the amounts of the drug-receptor complex in either the high affinity or low affinity forms, respectively. The drug-receptor complex can also exist in either an ionized ($DR_H$) form or non-ionized ($DR_L$) form. The non-ionized form is the lower affinity form. This characterization teaches that the protonation of at least one (class of) residue within the receptor alters the affinity of the drug for the two free states of the receptor. The $K_R$ term is the dissociation constant of the hydrogen ion ($H^+$) binding to the receptor in the absence of the drug. The $K_{RD}$ term is the dissociation constant of hydrogen ion ($H^+$) binding to the receptor in the presence of the drug.

The drug (or ligand) binding to each of the two receptor states can be described by the Langmuir binding expressions:

$$DR_H = R_H(D)/((D)+K_{DH}) \text{ and } DR_L = R_L(D)/((D)+K_{DL})$$

where $DR_H$ and $DR_L$ are the amounts of the drug-receptor complex for the high and low affinity states, respectively; and, $R_H$ and $R_L$ are the total amounts of the receptors in the high and low affinity states. The ligand will have a preference for binding to the high affinity receptor state, $R_H$, over the low affinity receptor state, $R_L$, which is a direct result of the different dissociation constants $K_{DH}$ and $K_{DL}$. Any differences in the affinities of a ligand for the two receptor states produces a "shift" in the receptor reaction quotient similar to Le Chatelier's Principle.

Now introducing a new term, $\Gamma$, as a ratio of the high affinity states of the receptor to the low affinity states, the following expression is obtained:

$$\Gamma=(R_H+DR_H)/(R_L+DR_L) \quad [1]$$

where $\Gamma$ is a "weighted ratio" of the two receptor states. By substituting the binding expressions for $DR_H$ and $DR_L$ the complete expression for $\Gamma$ can be described as:

$$\Gamma=R_H(1+(D/(D+K_{DH})))/R_L(1+(D/(D+K_{DL}))) \quad [2]$$

The derivation of equation [2] includes the assumption that the concentrations of the free receptor states ($R_H$ and $R_L$) are determined by the environmental influences on the protonation and deprotonation of the receptor and that the drug binding to each state can be described by Langmuir binding. Perhaps the closest physical analogy to elucidate this "weighted ratio" approach is that the receptor equilibrium may be considered analogous to a beam balance with weights. The addition of a ligand is comparable to the addition of weights to each side of the balance relative to a hypothetical affinity with one side having the more weight or "higher affinity". The weighted ratio would be the ratio of the original weight plus the additional weight on the "high affinity" side of the fulcrum divided by the original weight plus the additional weight on the "low affinity" side. Additionally, a second weighted ratio would be the distances of the centers of mass from the fulcrum. This second weighted ratio would comprise the original distances plus or minus the change in these distances that was necessary to maintain the horizontal equilibrium point. The two weighted ratios will be equivalent and similar to this analysis of the receptor response. Similarly a second or parallel determination of $\Gamma$ can be made from consideration of the conservation of matter law. This requires that any discrete change or increase (+x) in the high affinity state must be reciprocated by an equal and opposite change (-x) in the low affinity state with all receptor states equal to the total number of receptors ($R_T$). In this case, the equation for mass balance can be expressed as:

$$R_T=(R_H+x)+(R_L-x) \quad [3]$$

Therefore, the weighted ratio of the high to low affinity states can be alternatively expressed as:

$$\Gamma=(R_H+x)/(R_L-x) \quad [4]$$

and Equation [4] can be solved for the discrete change, x, which yields:

$$x=(\Gamma R_L-R_H)/(1+\Gamma) \quad [5]$$

The equivalence of equations [1] and [4] was tested numerically (not shown); also the expression for $\Gamma$ from equation [1] can be substituted into equation [5] and subsequently into equation [4] to produce the original expression for $\Gamma$. Equating the weighted ratios of the high and low affinity receptor states in terms of the ligand binding or the conservation of matter law does not appear to have been done before. Equating the two weighted ratios, equations [2] and [4], and solving for x yields:

$$\Delta RH = \frac{R_H R_L(D)(K_{DL} - K_{DH})}{R_L(2D + K_{DL})(D + K_{DH}) + R_H(D + K_{DL})(2D + K_{DH})} \quad [6]$$

where $\Delta R_H$ is substituted for x, in order to emphasize that it represents the change in the high affinity state.

Taking the first derivative of the above equation with respect to the dose, D, and setting it equal to zero in order to obtain the peak (maximum) curve yields the following expression for the concentration of the drug where this peak occurs:

$$D=(K_{DH}K_{DL}/2)^{1/2} \quad [7]$$

In the presence of an antagonist or inhibitor (I), the equilibrium constants, $K_{DH}$ and $K_{DL}$, will each be multiplied by $(K_i+[I])/K_i$ so that equation (7) becomes:

$$D=(K_{DH}K_{DL}/2)^{1/2}(K_i+[I])/K_i \quad [8]$$

If the concentration of the inhibitor (I) is expressed as a fraction (f) of the dose of the drug D, i.e., [I]=f[D], then substitution of this expression for [I] into equation (8) and solving for f yields:

$$f=K_i(D-\phi)/\phi D \quad [9]$$

where, $$\phi = (K_{DH} K_{DL}/2)^{1/2}$$

Observing that equation (9) gives the minimal fractional concentration of the inhibitor with respect to the drug that is necessary to prevent the desensitization of the receptor, it follows that as [D] becomes much larger than φ, equation (9) becomes:

$$f = K_i/\phi \quad [10]$$

This is the fractional dose of the antagonist relative to the concentration of the agonist or drug which is necessary and sufficient to prevent any desensitization of the receptor for the particular drug that is being used. This is refered to as the optimal ratio for any agonist-antagonist composition.

The instant formulation determines the lowest acceptable dose of inhibitor or antagonist to mix with the drug which completely prevents desensitization. It expresses the dose of inhibitor as a fraction of the dose of the drug. Further, the formulation prevents significant inhibition of the response at lower concentrations of the drug, yet prevents any of the desensitization of the receptor which is a direct result of the high concentrations of the drug (see FIG. 2).

Figure 2:
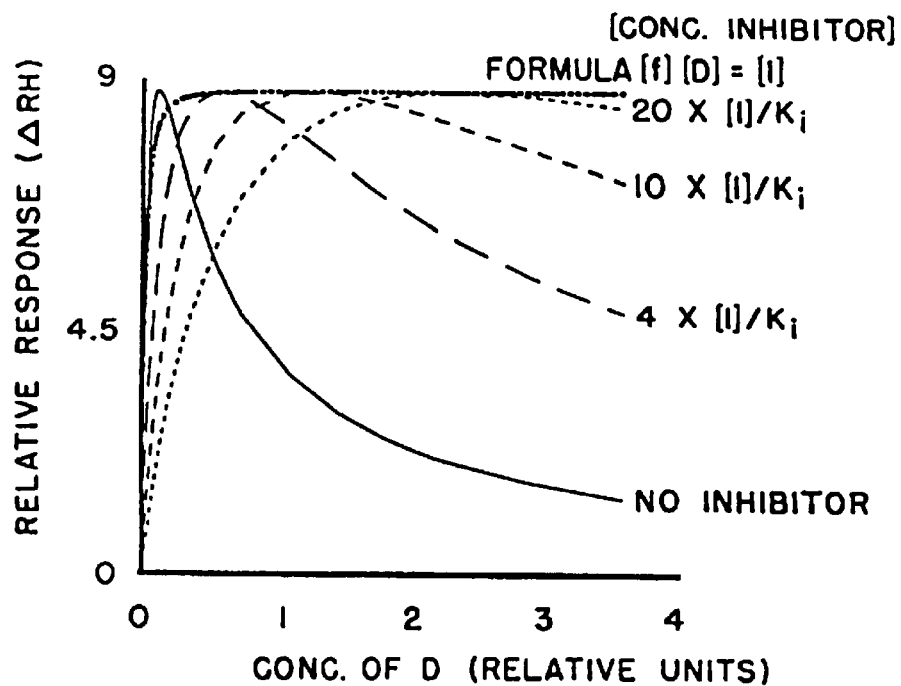
FIG. 2 is a graphical representation of Relative Response vs. Concentration for Different Concentrations of the Competitive Inhibitor, [I]

Referring particularly to FIG. 2 there is shown a graphical demonstration of the ability of the formulation f D=I to prevent desensitization without affecting the maximum response. Experimentally, computer simulations were carried out to demonstrate the ability of this model, equation [6], to describe a number of dose-response curves that were difficult or impossible to model by previous theories. Previously published experiments were compared to the predictions from this model. As an example, the experimental dose-response curves from del Castillo and Katz were described by equation (6) with and without an inhibitor (see FIG. 6).

Other experimentally determined curves have been described by my method including the more recent work of Keen (Keen, M., *Trends Pharmacol. Sci.* 12, 371–374 (1991)). The response curves from Keen are given in FIG. 4, wherein the darker curves are the computer generated curves from the model and fit those curves from the experiments and, whereas the lighter curves (generated from the prevalent operational model) failed to fit the experimental curves. Examples follow hereinafter in more detail, illustrative of the experimental development of my invention.

EXAMPLE 1

Stephenson's data (Stephenson, R. P., *British. J. Pharmacol.* 11, 379–393 (1956)) are presented in FIG. 3. The points on these curves were generated by equation [6]. The value for both of the $R_H$ and $R_L$ terms was 50 and the values of the pairs of $K_{DH}$ and $K_{DL}$ terms were as follows: Butyl ($3\times10^{-6}$, $8\times10^{-2}$); Hexyl ($5\times10^{-6}$, $2\times10^{-3}$); Ethyl ($1\times10^{-4}$, $1\times10^{1}$); Heptyl ($2\times10^{-5}$, $3\times10^{-4}$); Octyl ($3\times10^{-5}$, $2\times10^{-4}$); Nonyl ($4\times10^{-5}$, $2\times10^{-4}$); and Decyl ($3\times10^{-5}$, $2\times10^{-4}$). The concentration of drug [D] is represented on the abscissa in a molar log scale.

The reader will note that equation [6] can represent the experimental data from Stephenson with meaningful biophysical parameters (i.e. the two dissociation constants of the drugs for the two receptor states).

EXAMPLE 2

Referring once again to FIG. 4, the plots of $\Delta R_H$ (equation [6]–solid lines) for the data of Keen (Keen, 1991) are presented for arecoline, pilocarpine and carbachol as well as the plots of the operational model (broken lines). $\Delta R_H$ was calculated with 300 as the value for the $R_H$ and $R_L$ terms to scale the curves appropriately. The $K_{DH}$ and $K_{DL}$ terms were varied in order to model the experimental curves. The $K_{DH}$ and $K_{DL}$ values for arecoline were 2 and 2000 respectively; similarly, the values for pilocarpine were 4 and 220; and the values for carbachol were 0.02 and 1000.

The Equation to Calculate the Curves for the Operational Model:

$$\% \text{ response} = \frac{\alpha([R_O]/K_{AR})(D/K_A)}{1 + (1 + ([R_O]/K_{AR}))(D/K_A)}$$

where $([R_O]/K_{AR})$=16, 7.3, 3.5, 1.3 and 0.116 with α=100% (plotted as the broken lines in the graph). KA is the overall dissociation constant for the binding of the agonist to the receptor as defined in the operational model.

Figure 3:
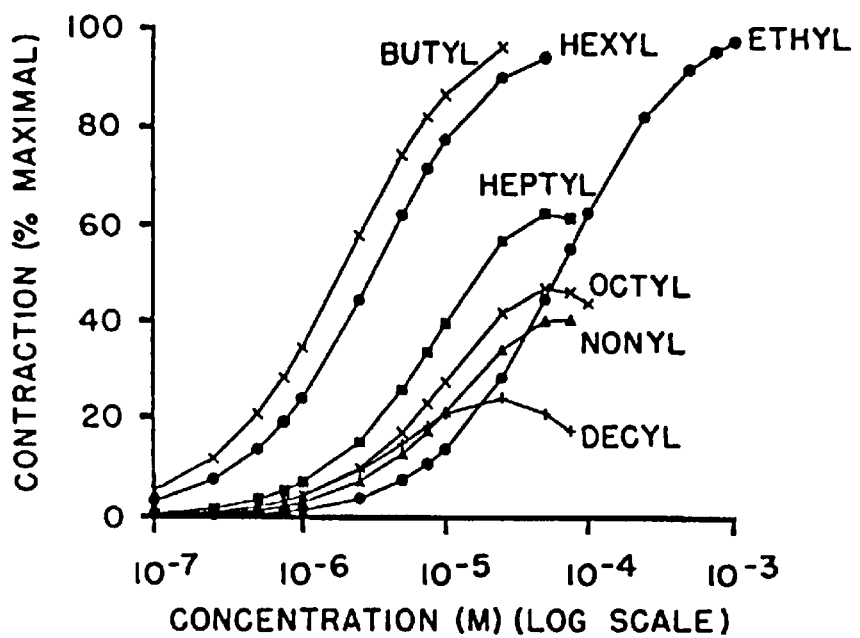
FIG. 3 reflects curves for the responses as determined by Stephenson.
Figure 4:
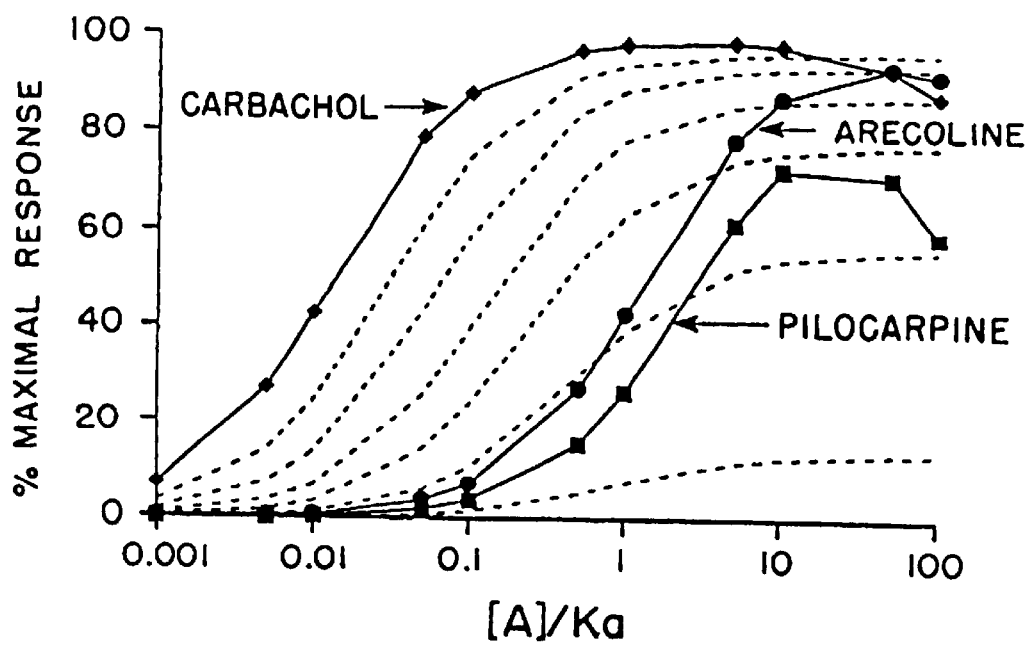
FIG. 4 is a model of ΔRH to the operational model and the data of Keen.

Experimentally determined response curves were examined to test the ability of ΔRH to model these curves. The experimentally determined dose-response curves from Keen (Keen, 1991) and Stephenson (Stephenson, 1956) were easily modeled by ΔRH from equation [6] with appropriately selected $K_{DL}$ and $K_{DH}$ values (FIGS. 3 and 4). Although there may be some tissue dependent effects from unstirred layers or diffusion barriers, no modifications were used in order to model these curves. Other curves were examined to test the ability of equation [6] to model these curves and to determine additional factors that may be necessary to model the total response.

Basically, there were two modifications to ΔRH that were necessary to model the experimental dose-response curves of Dilger and Brett (Dilger, J. P. and Brett, R. S., *Biophysical J.* 57, 723–731, (1990)) and del Castillo and Katz. The first modification was a diffusion equation to model the time-dependence of the ligand concentration at the receptors and the second modification was a "recruitment function" to model the concentration-dependent "diffusional recruitment" of additional receptors.

Most experimental preparations have multiple diffusion barriers or unstirred layers in the preparations which can cause time-dependent changes in the agonist concentration at the receptor sites. In order to account for this, the following diffusion equation was used:

$$[D]t = \frac{(D)10^{(t^*Q/r2)} - (D)}{10^{(t^*Q/r2)}}$$

where [D]t is the time-dependent change in agonist concentration. (D) is the applied concentration of the agonist; "t" is the time; "Q" is the diffusion coefficient of the agonist and "r" is the estimated average diffusion distance. With [D]t substituted for (D) in equation [6], a time-dependent response could be modeled. The diffusion expression appears necessary to describe a time-dependence to the experimental curves, but not the overall shapes of these curves.

Because the peak heights of some experimental curves vary with the applied dose of agonist, an additional modification to ΔRH was necessary to model these curves. Application of high agonist concentrations produce large peaks, whereas, lower agonist concentrations produce small peaks in the measured dose-response curves. This is not predicted from plots of ΔRH with or without a diffusion equation. One explanation for this phenomenon is that there is a concentration-dependent "diffusional recruitment" of receptors. Katz and Thesleff (Katz, B. and Thesleff, S., *J. Physiol.* 138, 63–80 (1957)) and more recently Cachelin and Colquhoun (Cachelin, A. B. and Colquhoun, D., J. Physiol.415, 159–188, (1989)) suggested that agonists may diffuse to distant receptors in their preparations and they proposed a concentration-dependent change in the total number of receptors as a necessary modification. The receptors which do not participate in the response at low agonist concentration may be either physically distant or separated by diffusion barriers within a particular preparation. This suggests that some of the receptors are removed from the initial site of agonist exposure but become "recruited" as the concentration of the agonist is increased. Because the experimental curves from Dilger and Brett have decreasing peak heights with decreasing agonist concentrations, a "recruitment function" was found necessary to modify ΔRH. This "diffusional recruitment" can be modeled approximately by a hyperbolic function which includes the ligand concentration and an apparent dissociation constant for the half maximal receptor recruitment.

$$R_F = \frac{R_M(D)}{(D) + KF}$$

where $R_M$ represents the relative maximum number of receptors and $K_F$ is the apparent dissociation constant for the concentration of acetylcholine which produces a half maximum of the peak height. $R_F$ adjusted the relative number of receptors contributing to the total response by multiplying ΔRH times $R_F$.

EXAMPLE 3

Figure 5:
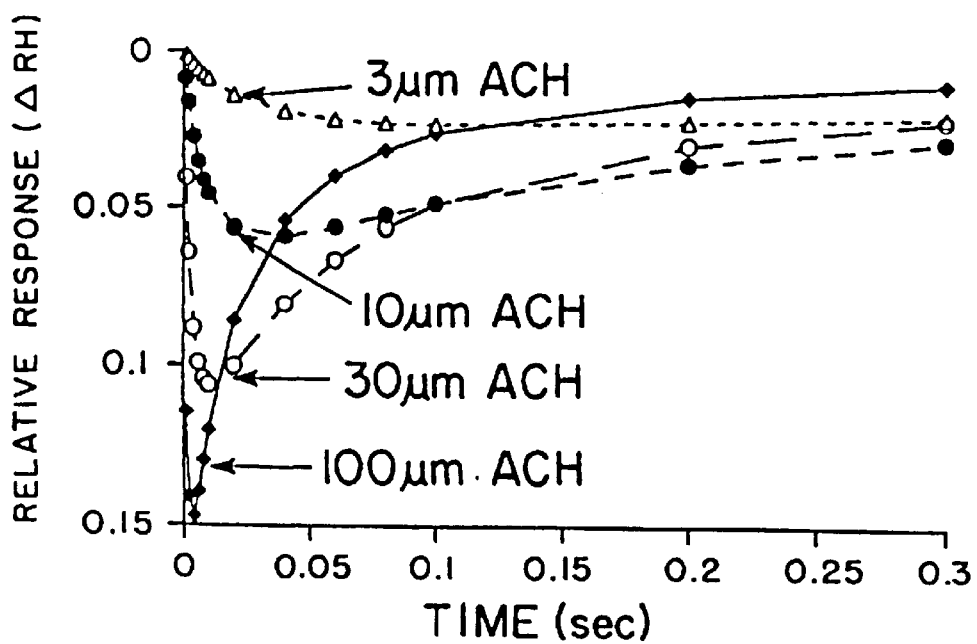
FIG. 5 is the response curves of Dilger and Brett modeled by ΔRH with a diffusion equation.

As depicted in FIG. 5, the response curves of Dilger and Brett are modeled by ΔRH with a diffusion equation, [D]t, to represent the change in concentration with time and a recruitment function, $R_F$, to describe the diffusional recruitment of receptors. The diffusion coefficient used for acetylcholine (ACH) is 6×10-10 m2s-1, which is a generally accepted value. The values for the $R_H$ and $R_L$ terms are one for this graph. The apparent affinity constant for the diffusional recruitment of receptors, $K_F$, is 20 μM as determined by the half maximal change in the peak heights of the experimental curves. Where "t" is the time in seconds and "900×10-12" is the square of the distance (30×10-6 m). The $K_{DH}$ and $K_{DL}$ values of acetylcholine are 0.01 and 0.1 respectively.
The series of equations to calculate ΔRH are:

$$R_F = 100D/(D + K_F)$$

$$[D]t = \frac{(D)10^{(t^*6\times10/900\times10)} - (D)}{10^{(t^*6\times10/900\times10)}}$$

$$DR_H = \frac{R_H[D]t}{[D]t + K_{DH}}$$

$$DR_L = \frac{R_L[D]t}{[D]t + K_{DL}}$$

$$\Gamma = \frac{R_H + DR_H}{R_L + DR_L}$$

$$\Delta RH = \frac{R_F(\Gamma R_L - R_H)}{1 + \Gamma}$$

where the last four equations are operationally equivalent to equation [6] for ΔRH. The effect of a competitive inhibitor on the response curves can be modeled by including the expressions for competitive inhibition into the Langmuir binding expressions for $DR_H$ and $DR_L$ and then substituted into equation [5], so that the weighted ratio becomes:

$$\Gamma = \frac{R_H(1 + (D/(D + K_{DH}(1 + I/K_i))))}{R_L(1 + (D/(D + K_{DL}(1 + I/K_i))))}$$

where "$I/K_i$" is the concentration of the inhibitor divided by the dissociation constant of the inhibitor for the receptor. The effect of an antagonist or competitive inhibitor on the response curve shows that when the inhibitor is present the slope of the response curve on the descending side diminishes more than the slope on the ascending side of the curve which is similar to the experimental observations of del Castillo and Katz as well as Geofroy et al.

EXAMPLE 4

Figure 6:
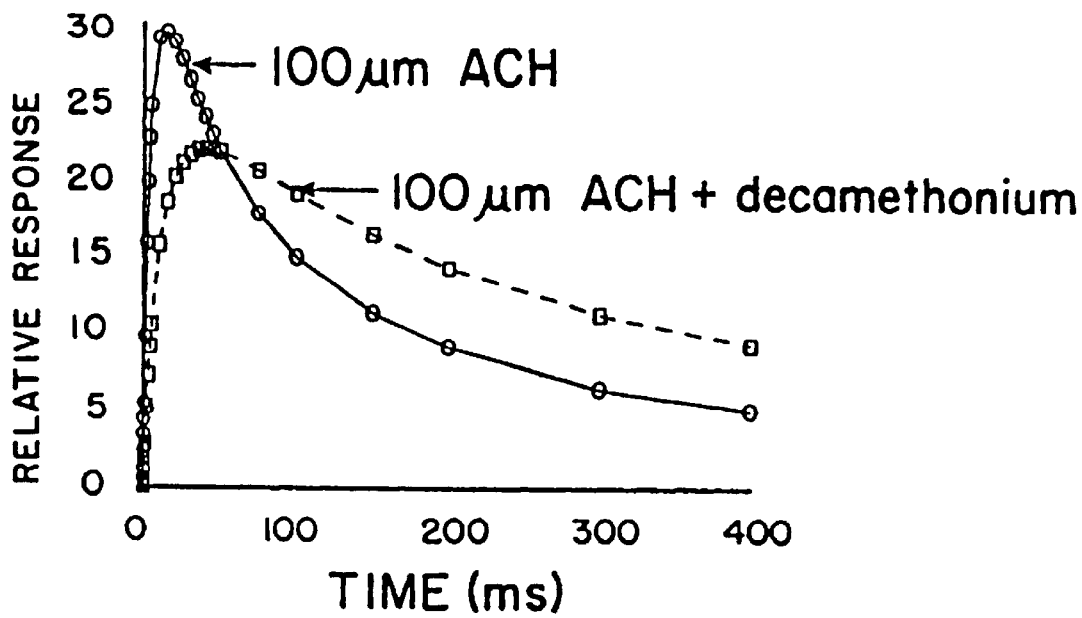
FIG. 6 is an experimental dual plot modeling: del Castillo and Katz dose-responses.

FIG. 6 consists in the two plots of ΔRH which model the experimental dose-response curves of del Castillo and Katz. ΔRH is computed by the series of sequential equations shown below. The values for the $R_H$ and $R_L$ terms are 100. The initially applied concentration of acetylcholine (ACH) was 100 μM. The values for the maximum peak response of acetylcholine (100 μM) and half maximal peak response (20 μM) were taken from Dilger and Brett for use in the recruitment function, $R_F$. The effective diffusion distance in [D]t is 191 μm and "t" is the time in seconds which is converted to milli-seconds for the plot. The inhibitor concentration for decamethonium, expressed as $I/K_i$ is equal to either 0 or 1 ([I]=$K_i$) for the two plots. The recruitment function, $R_F$, also includes the effect of the competitive inhibitor. Decamethonium, which was a weak partial agonist in the hands of del Castillo and Katz, is treated as a competitive antagonist without any contribution to the response.
The series of equations to calculate ΔRH:

$$R_F = \frac{200(D)}{(D) + K_F(1 + I/K_i)}$$

$$[D]t = \frac{(D)10^{(t^*6\times10/364\times10)} - D}{10^{(t^*6\times10/364\times10)}}$$

$$DR_H = \frac{R_H[D]t}{[D]t + K_{DH}(1 + I/K_i)}$$

$$DR_L = \frac{R_L[D]t}{[D]t + K_{DL}(1 + I/K_i)}$$

$$\Gamma = \frac{R_H + DR_H}{R_L + DR_L}$$

$$\Delta RH = \frac{R_F(\Gamma R_L - R_H)}{1 + \Gamma}$$

To apply the instant methodology to a specific case requiring administration of a drug to a human subject according to a commonly accepted protocol (state of the art), one first obtains the drug's dose-response curve that is provided by the drug's maker or are experimentally determined. The curve is then "fitted" by normalizing for the total number of receptors and optimizing the values for the high and low affinity constants $K_{DH}$ and $K_{DL}$. These fitted values are the entering biophysical arguments for the calculation of φ and f, according to this specification, which results in the optimal ratio of the antagonist with respect to the drug-agonist (antagonist: agonist) that is necessary to prevent desensitization of the receptor. The administration of antagonist is by normal delivery methods of its own character and may be done during the agonist administration or, if such is autonomic in the recipient, concurrent therewith, or shortly thereafter. Agonists and antagonists are made into pharmaceutical compositions by combinations with appropriate medical carriers or diluents. For example, such mixtures can be dissolved in oils, propylene glycol, physiological saline, isopropyl myristate, ethanol, cremophor, glycol, sesame oil, or other such pharmacological solutions. Formulation as topicals is also available. Pharmacologists familiar with the panoply of drugs and their professional literature may readily use the invention with the guidance herein provided.

As a result of numerous in vivo studies and my biophysical models, several antagonist/agonist pairings of any of the possible combinations of a beta-1-agonist with any of the possible beta-1-antagonists (or partial agonists), in the ratios taught herein, include without limitation: isoproterenol/acebutalol; isoproterenol/atenolol; isoproterenol/labetalol; isoproterenol/metoprolol; isoproterenol/nadolol; isoproterenol/oxprenolol; isoproterenol/pindolol; isoproterenol/propranolol; isoproterenol/sotalol; and isoproterenol/timolol. Similar compositions are made for each of the following beta-1-agonists: adrenaline; dobutamine; epinephrine; ephedrine; metaproteronol; norepinephrine; noradrenaline; and xamoterol, for example: dobutamine/propranolol; dobutamine/atenolol; dobutamine/betaxolol; dobutamine/metoprolol; dobutamine/timolol; dobutamine/sotalol; dobutamine/pindolol; dobutamine/betaxolol; norepinephrine/atenolol; ephedrine/timolol; epinephrine/sotalol; noradrenaline/pindolol; xamoterol/betaxolol; and metaproteronol/propanolol, to name but a few such beta-1-agonist/antagonist combinations. The invented compositions include all drugs or molecular entities capable of acting as either beta-1-antagonists or beta-1-agonists as the molecular entities to be used in making these compositions; and they also include the use of the enantiomers of the beta-1-antagonists and beta-1-agonists as the working molecular entities.

Initial Experiment

Figure 7:
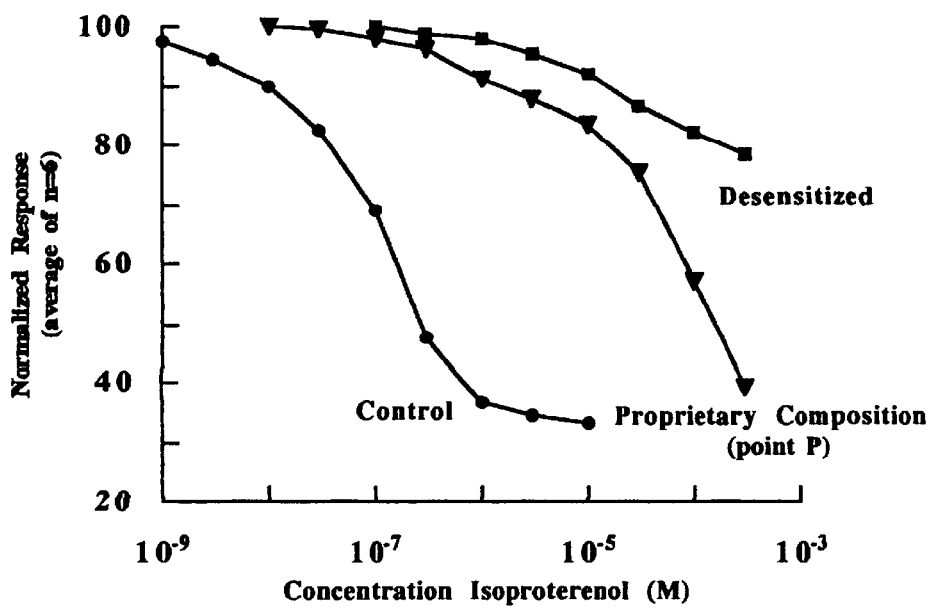
FIG. 7 presents empirical data obtained for in-vitro studies on carbachol-contracted Guinea pig trachea.

FIG. 7 provides in vitro experimental data (CEREP, CELLE L=EVESCAULT, France rpt. No. 1124 R 820E), which verify my "optimal ratio method" to determine a specific agonist/antagonist composition to prevent β2 receptor desensitization. The inhibitor constant $K_i$, was first determined for two concentrations of propranolol (1.0 μM and 10.0 μM) measured on the desensitized preparations. The value for $K_i$ was $2.96 \times 10^{-7}$ M. This low value is reasonable because the tissues were treated with 30 μM of the catechol-O-methyl transferase inhibitor U-0521 which was added for forty-five minutes prior to exposure to isoproterenol (the agonist) or propranolol (the antagonist) and present thereafter. This "blunting" of the $K_i$ has been previously observed in the presence of metabolic inhibitors. The value of the maximum of the control curve was calculated from a fit of the curve as previously described in this disclosure. This value was calculated from $\phi=(K_{DL}K_{DH}/2)^{-1/2}$ and found to be $7.48 \times 10^{-6}$ M. It also agreed with a measured estimate from the experimental points. In order to calculate the fraction of inhibitor necessary to prevent receptor desensitization, the following was calculated: $f=K_i/\phi$ and found to be $3.95 \times 10^{-2}$ which is in excellent agreement with the experimentally determined values of 1.0 μM propranolol/25.0 μM isoproterenol which gives f=0.04. Thus, this experiment confirmed the preparation of an optimal ratio made according to the herein disclosed method. In determining the optimal ratio of propranolol to isoproterenol in order to prevent the isoproterenol-induced desensitization in the Guinea pig isolated trachea, it was noted that other concentrations of propranolol (0.2 and 10.0 μM) that were tested experimentally, were found to be ineffective in restoring the maximum response of the tissue. These results prove valid my initial hypothesis, and later assertion, that there is a maximally effective ratio which will provide the intended results since the concentrations of the propranolol were either smaller or larger than the 1.0 μM found to be optimal for this system.

The conclusions garnered from this specific test show that the invention is logically extendable to include other agonist-antagonist pairs on other receptors which display desensitization or fade. Since propranolol has been labeled as a "negative antagonist" or an "inverse agonist", those ligands labeled as negative antagonists or inverse agonists would be included in the term "antagonists" within the meaning of this disclosure. Additionally, these compositions can be seen to reverse previously desensitized receptors. The logical extensibility of my invention to include other agonist-antagonist pairs on other receptors and the fact that these compositions can reverse previously desensitized receptors are further militated by a detailed reading of the incorporated references which, although not anticipatory or suggestive of the instant methods and compositions, nonetheless provide data which may be analyzed to infer confirmation of my teachings.

Experiments for Cardiac Desensitization

Figure 8:
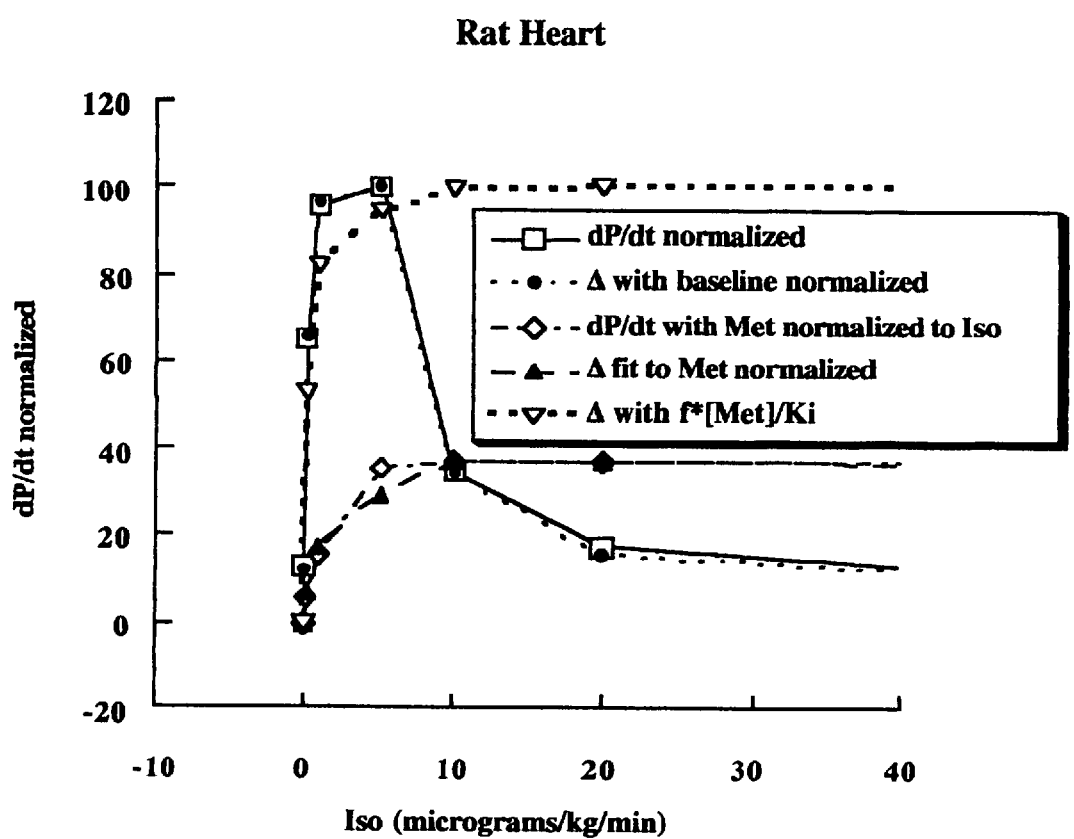
FIG. 8 is a graphical fit of the calculated data (Δ-delta) to the experimental data (dP/dt) for the agonist (isoproterenol), with and without a fixed amount of the antagonist (metoprolol)
Figure 9:
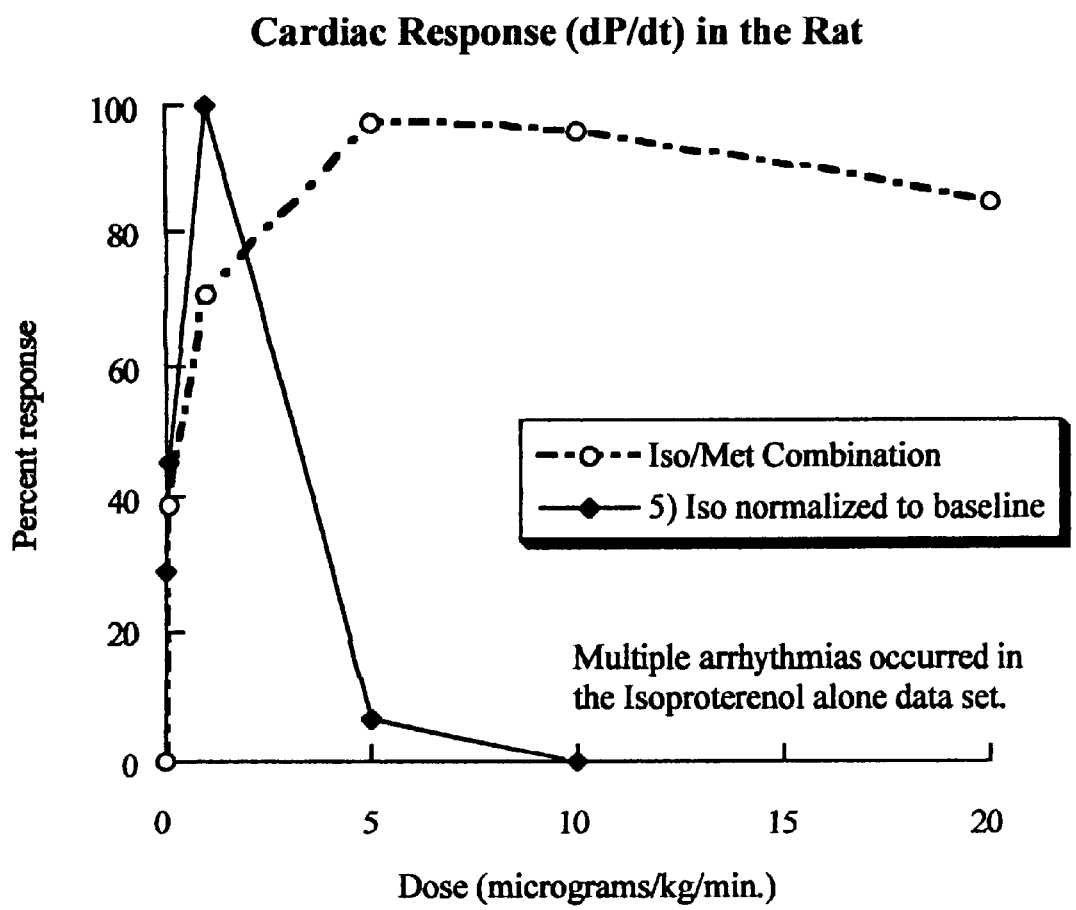
FIG. 9 is a plot of the experimental response in the test animals to the calculated optimal ratio of agonist/antagonist (Iso/Met Combination) derived from the biophysical parameters obtained from fitting the test dosages in FIG. 8 to the equations 6–10.

There was made a fit of the experimental data for the agonist (showing the expected desensitization) with and without the antagonist (at a fixed concentration) to the theory (Δ or ΔRH from equations 1–10. Referring to the first graph, FIG. 8, labeled "Rat Heart", this was created by fitting the experimental data for the isoproterenol (Iso) alone to the equations 1–10. This was done both with and without a fixed amount of metoprolol (Met) (1 mg/kg/min) to determine the $K_i$ for the antagonist, Met. The experimental points for Iso alone are labeled "dP/dt normalized" and the fit based upon theory is labeled "with baseline normalized". In the presence of the fixed amount of the antagonist, Met, the experimental points are labeled "dP/dt with Met normalized to Iso" and the fit based upon calculation is labeled "fit to Met normalized". The last curve displayed is the projected curve for the optimal composition which is labeled "with f*[Met]/$K_i$". The $K_{DH}$, $K_{DL}$ and $K_i$ were obtained from this fit and put into the final equation for "f" (the fraction of the dose of the antagonist to use with respect to the agonist). From the fit, the values obtained were $K_{DH}$=19.0; $K_{DL}$=1.3 and $K_i$=300 micrograms/kg/min. These values were substituted into the equation for f, which yielded 85 to the nearest integer as the optimal ratio. For each microgram amount of isoproterenol, was mixed 85 micrograms of metoprolol and experimentally tested; this is shown in FIG. 9, the graph labeled "Cardiac Response (dP/dt) in Rat". Therefore, the optimal ratio was 1:85, Iso:Met. This is the ratio which was used to generate the second curve, labeled "Iso/Met Combination".

Summary of the Experiments to Test the
Combination of Beta-1-Agonists with Antagonists
to Prevent Desensitization Background Isoproterenol (Isuprel) and dobutamine are two drugs commonly used today in patients with decreased cardiac output and heart failure. Both are sympathomimetic adrenergic agonists that bind beta-adrenergic receptors and thus promote increased heart rate and contractility.

Metoprolol (Lopressor) is conversely a beta-adrenoreceptor blocking agent that selectively blocks the beta-1-receptors and is frequently prescribed for heart failure.

The time-derivative of the blood pressure in the ventricle of the heart (dP/dT) is an accepted measurement of the contractility of the heart: as the strength of the contractions in the ventricle of the heart goes up, the rate at which the pressure in the ventricle rises will increase. Increased dP/dT therefore implies increased contractility.

Consequently it was proposed that, by infusing an adrenergic agonist in a specific combination with a beta-1-receptor blocker (see U.S. Pat. No. 5,597,699 ('699)) and measuring the resultant left ventricular pressure (LVP) and dP/dT, it would be possible to induce and measure an increased contractility and cardiac output without suffering a corresponding increase in desensitization.

All beta-1-receptor experiments were performed by Gwathmey, Inc. (Boston).

Hypothesis

An undesired side effect that accompanies the use of adrenergic agonists Isoproterenol (Isuprel) and dobutamine is desensitization. In addition, these drugs also produce an increase in heart rate (tachycardia) and arrhythmias. It was proposed that, if these drugs are combined and administered in an optimal ratio as calculated by '699, then the desensitization will be markedly diminished or absent. The agonistic effects of isoproterenol and dobutamine will produce increased contractility with a better therapeutic response; a sustained contractility and possibly reduced arrhythmogenesis with the combination drugs (isoproterenol+metoprolol=Iso+Met or dobutamine+metoprolol=Dob+Met) than with either drug alone (Iso or Dob).

Methods

Isoproterenol (Iso) and dobutamine (Dob) were tested in vivo with and without the beta-1-antagonist, metoprolol (Lopressor)(Met).

For each of the following experiments, a rat weighing from two hundred to three hundred grams was anesthetized by intraperitoneal (IP) injection of 75-mg/kg sodium pentobarbital (Sodium Nembutal). Following sedation, the neck of the rat was incised and a tracheotomy was performed, inserting a 14-gauge angiocatheter sheath into the trachea of the rat and securing it with a silk tie. The angiocatheter was connected through a small tube to a small animal respirator supplied with 1.0 liters of oxygen per minute and set to 95 breaths per minute.

The right carotid artery was next tied off, and after making a small incision, a Micro-Tip Millar pressure catheter was introduced down through the carotid artery, placing the end of the catheter into the left ventricular cavity of the rat's heart. Position of the catheter tip was determined by the waveform of the pressure reading-placement in the left ventricle was presumed when a diastolic pressure of zero mmHg and a reasonable systolic pressure (70 to 150 mmHg) was observed. Once properly placed, the catheter was secured to the artery with 1–0 silk ties.

Following placement of the Millar catheter, the right jugular vein of the rat was tied off and cannulated by incising the side of the vein and introducing a small (0.3 mm internal diameter), 20 centimeter-long intracatheter pre-loaded with 0.9% saline solution into the vein. Once a reasonable length of the catheter was inserted into the vein, it was tied to the vein with 1–0 silk suture to secure it in place.

The Millar pressure catheter was then connected through a Millar transducer control unit to a digital/analog recording card in a Sonometrics computer. The transmitted Millar pressure signal was then zeroed and calibrated in the Sonometrics SonoLAB data acquisition program.

At this point for each rat, a baseline recording was obtained of the left ventricular pressure tracing. Segments of three to five seconds were recorded, and it was from these recorded tracings that the included figures of maximum left ventricular pressure (reported as LVP), maximum time-derivative of left ventricular pressure (dP/dT), and heart rate (HR) were later determined, by analysis with Sonometrics CardioSOFT data analysis software.

At this point in the experimentation, the procedure followed differed depending upon which drugs and mixtures were being examined, as is described in the following paragraphs.

The IV line was connected to a syringe of isoproterenol (Isuprel) or dobutamine in solution on a fluid infusion pump. The isoproterenol was administered at varying rates (see figures); at each rate the LVP tracing was recorded after several minutes at a constant infusion rate, and the tracing was later analyzed in the same manner as described above for the baseline LVP recordings. The same procedure was then performed in the rats using a solution of metoprolol alone. Again, at each rate, LVP was recorded for later analysis. The procedure was repeated a third time, except that infusion rate of isoproterenol was varied while at the same time a constant dosage of metoprolol (1 mg/kg/min) was administered. This constant dose is not the calculated ratio, but served to calculate an accurate $K_i$ for metoprolol in these rats.

In the Iso exposed rats, there were a set of experiments done where the rats served as their own controls. In these experiments the rats were first given Iso alone to either 20 microgram/kg/min dosages or until arrhythmias occurred. They were then allowed to rest and given the Iso+Met combination up to either 20 microgram/kg/min dosages or until arrhythmias occurred. The dP/dt observations were recorded for each infusion.

In rats 1 through 7, dobutamine solution was first infused at varying rates and LVP tracings were recorded. In these experiments, the rats were first infused with a low-concentration solution (for accuracy of administered dosage). After the rate of dobutamine administration had progressed ~50 to 100 times the initial dosage, the solution was switched to a high-concentration (ten time as concentrated as the low-concentration) solution of dobutamine. This was done to avoid over-loading the rats with too much fluid volume. After completion of the dobutamine infusion in rats 1 through 7, the rats were then infused with a metoprolol solution, at the rates seen in the attached data tables (not shown). LVP was again recorded for later analysis at each infusion rate.

In rats 8 through 11, the rats were infused with the combination solution of dobutamine and metoprolol, in the calculated ratio of 1.0 mg dobutamine to 1.6 mg metoprolol. Infusion rates are displayed in the attached data; LVP tracings were taken at each rate. As was done in the straight dobutamine infusions in rats 1 through 7, the Dob+Met combination was switched from a low-concentration solution to a ten-times more concentrated solution (after the dosage of 100 times the initial dosage), again to avoid over-loading the rat with fluid volume.

Upon completion of each experiment, the rats were euthanized by intravenous (IV) overdose of sodium pentobarbital (75 mg/kg).

Results

Initially, the data obtained from the rats given isoproterenol alone were fit to the theoretical calculations and are presented in FIG. 9. In order to compare these data sets it is routine in pharmacological practice to zero and normalize each set of data to a common baseline so that the data can be compared and analyzed. As can be seen in the graph (FIG. 9: Iso normalized to baseline), with increasing administration of Iso, the dP/dT increased at low dosages, but peaked and rapidly decreased at higher dosages (desensitization), at the same time increasing the number of arrhythmias produced in the heart. The theory fit the experimental data very well with reasonable biophysical parameters (see FIG. 11 in the conclusion).

These experiments performed initially on the rats were done in order to determine the biophysical parameters (KDH, KDL and Ki) for calculating the optimal combination of a beta-1-agonist with antagonist according to the patent, '699. Based on these data, the combination of 1.0 mg isoproterenol with 18 mg metoprolol was calculated, and then tested in rats 5 through 7. Whereas for the dobutamine tests, the combination of 1.0 mg dobutamine with 1.6 mg metoprolol was calculated, and then tested in rats 8 through 11.

Next presented are the data from rats (5–7) tested with the composition Iso+Met in the graph in FIG. 9 titled "Cardiac Response (dP/dt) in the Rat" (Iso/Met combination). When the two were combined, it can be seen that the same increase in dP/dT was observed at low dosages of isoproterenol, but at higher dosages the dP/dT leveled off at an elevated level, rather than decreasing sharply (no desensitization occurred with the combination–Iso+Met). As seen in this graph (FIG. 9), the Iso+Met combination showed a better therapeutic response with a sustained response into the range of concentrations where desensitization would have normally occurred. In addition, there were much less arrhythmias observed in the Iso+Met run than in the Iso alone run.

Next presented are the data from the rats (4–7) treated with dobutamine alone (Dob), in which first dobutamine and then metoprolol alone were administered. Similar to the effects observed with the isoproterenol administration, it can be seen in the graph (FIG. 10: (Dob)) that at low dosages of dobutamine, the dP/dT increased; however at higher dosages the dP/dT again began to decrease (desensitization). With administration of metoprolol alone, there was observed a steadily larger decrease in dP/dT with every increasing dosage administered (not shown). In these seven rats, LVP was also recorded for each rat, and the graphs (not shown) show an effect in LVP parallel to the respective effects in dP/dT with administration of dobutamine or metoprolol alone. Administration of metoprolol alone served as a control to demonstrate that the metoprolol was acting as a β-1 antagonist in these animals.

In rats eight through twelve, the calculated combination of 1.0 mg dobutamine to 1.6 mg metoprolol was administered. Although these rats were given final dosages as high as 8,000 micrograms/kg/min and cumulative dosages estimated to be as high as 70,000 to 90,000 micrograms/kg, they functioned relatively well up until dosages past 1,000 micrograms/kg/min or estimated cumulative dosages of about 10,000 to 20,000 micrograms/kg. At the highest dosages past 1,000 micrograms/kg/min, dP/dt, LVP and heart rate (HR) all declined.

There were several possible reasons for the decrease in heart contractility at these extremely high dosages. First, the toxic level reported for the dobutamine LD50 i.v. in mice is 73 mg/kg (Merck Index p. 3453 (1996)); therefore, the rats were within this range where the toxic effects of dobutamine overwhelm any therapeutic effects and lead to the decline in the viability of the animals. Second, the problem with excessive fluid administration is problematic in these small animals; leading to electrolyte abnormalities and cardiac arrhythmias on the basis of too much fluid within the cardiovascular system. Given these caveats, the data for the Dob+Met rats were taken up to the 1,000 microgram/kg/min dosages and compared to the Dob only rats that were given dosages up to 800 microgram/kg/min.

Figure 10:
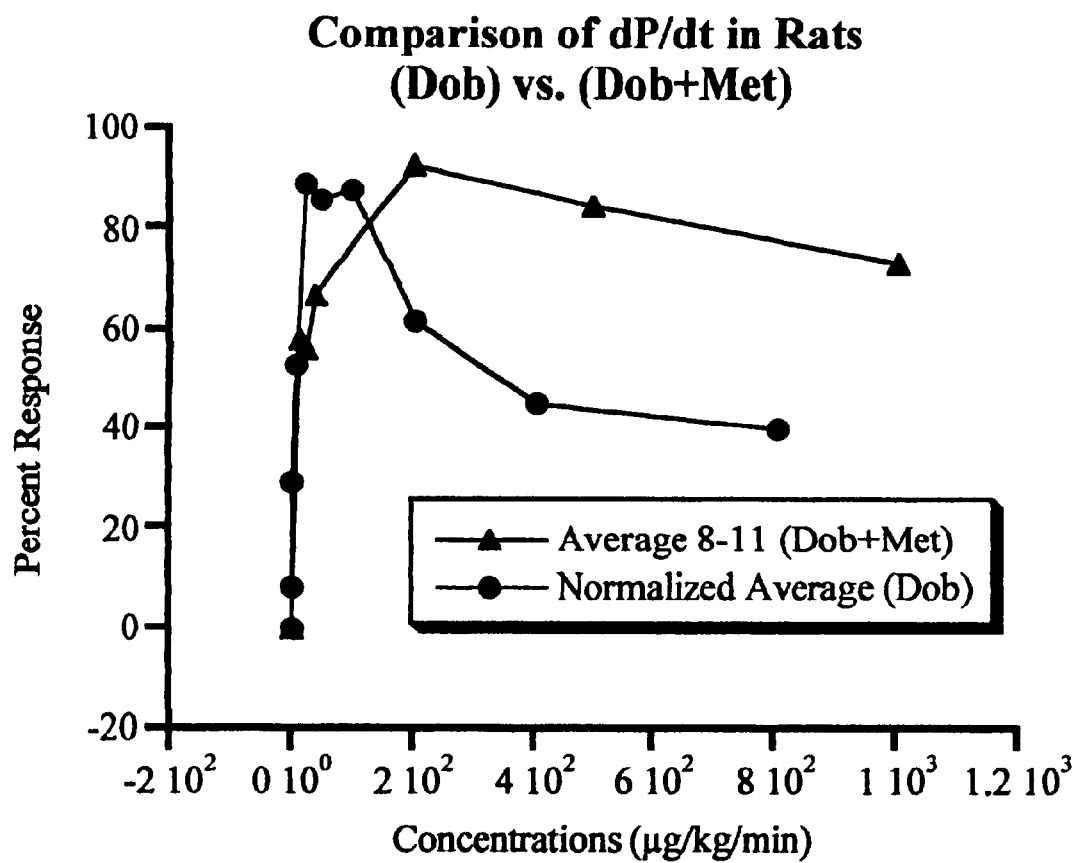
FIG. 10 is a graphical comparison of the experimental dP/dt in rats for dobutamine alone (Dob) versus the optimal ratio combination of dobutamine/metoprolol (Dob+Met)

Taking each set of data zeroing to a baseline and normalizing so that the data can be compared, is routine in pharmacological practice. The normalized averages for each set were compared in FIG. 3 below. For the Dob+Met group it can be seen that the response was maintained throughout the range; whereas, the Dob group showed a decline in response (see FIG. 10). As can be seen in FIG. 10, as the rate of administration of Dob was increased, dP/dT first increased, then peaked, and began to decrease at high dosages (desensitization). A similar effect was observed in the LVP-first an increase, a peak, a slight decrease that leveled off and finally a continued decrease at extremely high dosages. It is important to note however that the peaks in the dP/dT and LVP graphs do not correlate: in fact, the peak in the dP/dT graph came at a point when the LVP levels had returned to baseline. The graph of heart rate versus infusion rate shows that heart rate remained constant until extremely high levels of infusion, at which point the heart rate began to decrease swiftly which could have been due to the toxic effects of the drug at these high dosages.

Conclusions

When considering the raw data representing the isoproterenol tests, one can see that while infusing the combination of Iso+Met may have slightly diminished the absolute action of increasing dP/dT, the percentage change in dP/dT from baseline was largely matched by this mixture. One can also see that while high doses of pure isoproterenol resulted in a decreased dP/dT (desensitization), dP/dT during administration of the combination Iso+Met leveled off at an elevated level (no desensitization) which was sustained into the higher dosages where desensitization would normally occur. This effect suggests promise for the possibility of administering dosages of isoproterenol without having to worry about a dramatic decrease in the contractility of the heart or the potentially fatal increase in cardiac arrhythmias.

From these graphs (see FIGS. 9 and 10), one can see that the combinations Iso+Met or Dob+Met quickly increased dP/dT at low dosages, before stabilizing it at higher dosages. While LVP was first increased at low dosages, it stabilized at baseline levels for the higher dosages. Heart rate remained largely unaffected. These results are exciting in that they suggest that if the right combination of dobutamine and metoprolol is administered, it may indeed be possible to increase dP/dT (i.e. contractility, and thus cardiac output) without affecting the blood pressure or heart rate in the patient. In all, these experiments present exciting prospects for the hope of improving cardiac output without drug desensitization, arrhythmogenesis or tachycardia.

At the higher drug concentrations, there may occur a number of effects that include toxicity; excess fluid administration and electrolyte abnormalities. Although there was no mention made of arrhythmias, these rats appeared to maintain a very high output level over a long time. Although further testing should be done, it appears that these experiments support the hypothesis that desensitization can be reduced or eliminated in the β-1 agonist drugs by combining a β-1 antagonist with the agonist in the proper ratio to allow these drugs to increase contractility of the heart with a better therapeutic response; a more sustainable response and less cardiac arrhythmias.

Figure 11:
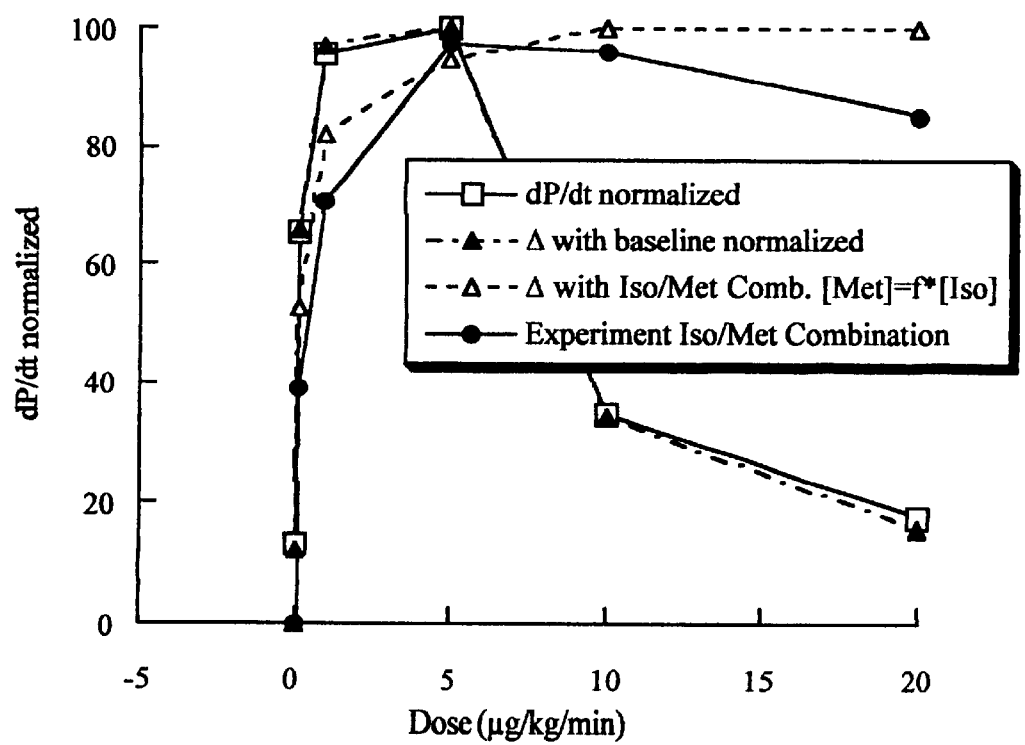
FIG. 11 is a graphical comparison of the fit of theory (Δ-delta) to the experimental results (dP/dt normalized and Experiment Iso/Met Combination) in vivo.

Finally in considering the ability of the theory from '699 to fit the experimental data, there were essentially three tests of the theory in these experiments. First, the theory was used to fit the initial experimental observations with Iso or Dob alone; Met alone and a fixed amount of Met with Iso or Dob. Second, the biophysical parameters derived from the initial fit ($K_{DH}$, $K_{DL}$ and $K_i$) were used to calculate a specific ratio as given in '699. Third, the experiments were conducted with and without the calculated combination and the observations were examined for their fit to the expected values. As seen in FIG. 11, the theory (Δ) fit the experimental data very well.

The administration of antagonist is by normal delivery methods of its own character and may be done during the agonist administration or, if such is autonomic in the recipient, concurrent therewith, or shortly thereafter. It is also well known that agonists and antagonist can be made into pharmaceutical compositions by combinations with appropriate medical carriers or diluents. For example, such mixtures can be dissolved in oils, propylene glycol, physiological saline, isopropyl myristate, ethanol, cremophor, glycol, sesame oil, or other such pharmacological solutions.

Formulation as topicals is also available. Pharmacologists familiar with the panoply of drugs and their professional literature may readily use the invention with the guidance herein provided.

This more physiologically subjective (and practical) method, and the compositions derived thereby, constitute effective and significant improvements to my original work. They are commended to the field consistent with the hereinafter appended claims.

What is claimed is:

1. A formulation containing an optimally effective ratio of an antagonist mixed with an agonist and comprising:
   a first amount of agonist-ligand effective for acquiring a desired, specific response from said receptors; and
   a second amount of antagonist-ligand, sufficient to prevent desensitization, maximize and sustain said response throughout an application of said formulation.

2. The formulation of claim 1 wherein the antagonist and the agonist form a defined antagonist/agonist pairing specific to and within a cellular receptor class.

3. The formulation of claim 2 wherein an antagonist/agonist pairing is selected from the group consisting of propranolol/isoproterenol; atenolol/norepinephrine; metoprolol/dobutamine; timolol/ephedrine; 2-amino-5-p phospho-nopentanoic acid/N-methyl-D-aspartic acid; progesterone/oxytocin; sotalol/epinephrine; pindolol/norepinephrine; betaxolol/xamoterol; and propanolol/terbutaline.

4. The formulation of claim 2 wherein the pairing further comprises enantiomers of beta-1-antagonists and beta-1-agonists.

5. A formulation that elicits a desired response from cellular receptors, prevents subsequent desensitization and sustains a maximal response of said receptors, comprising an agonist suitable for eliciting said response in a first amount effective for binding to said receptors in both a high and a low affinity state effective for obtaining said response mixed with an inhibitor of said agonist specific to said receptors, said inhibitor in a second amount sufficient to prevent desensitization and maintain the response of said receptor, said second amount being $K_i(K_{DL}K_{DH}/2)^{-1/2}$ the first amount, where $K_{DL}$ and $K_{DH}$ are dissociation constants of said agonist-ligand, and $K_i$ is the dissociation constant of said antagonist-ligand.

6. The formulation of claim 5, wherein said inhibitor is selected from the group consisting of partial antagonists, antagonists and competitive antagonists to said agonist.

7. A formulation that elicits a desired response from a cellular receptor while preventing subsequent desensitization of and sustaining a maximal response by said receptor and consisting essentially of:
   a first amount of an agonist ligand effective for eliciting said response and suitable for ligand binding to said receptor to both high and low affinity states; and
   a second amount of an antagonist ligand effective for sustained maximization of said response and for preventing desensitization of said receptor to the agonist ligand by binding partially in said second amount to said receptor substantially in said high affinity state to compete with the agonist ligand for said both slates.

8. The formulation of claim 7, where said second amount is $K_i(K_{DL}K_{DH}/2)^{-1/2}$ the first amount, where $K_{DL}$ and $K_{DH}$ are dissociation constants of said agonist-ligand, and $K_i$ is the dissociation constant of said antagonist-ligand.

9. A formulation containing an optimal ratio of an antagonist mixed with an agonist for preventing desensitization of agonist-specific cell receptors and maximizing response by said receptors comprising:
   a first amount of agonist effective for acquiring a desired response from said receptors; and
   a second amount of antagonist effective for inhibiting said response, said second amount being in a ratio to the first amount of the dissociation constant of said antagonist divided by the square root of half the product of high affinity and tow affinity dissociation constants of said agonist.

10. The formulation of claim 9, wherein said antagonist is selected from the group consisting of partial antagonists, antagonists and competitive antagonists to said agonist.

11. A formulation that elicits a desired optimal response from a cellular receptor while preventing subsequent desensitization of said receptor and consisting essentially of:
    a first amount of an agonist-ligand effective for eliciting said response and suitable for ligand riding to said receptor to both high and low affinity states; and
    a second amount of an antagonist-ligand, effective for sustaining a maximization of said response and preventing desensitization of said receptor to the agonist-ligand by binding partially in said second amount to said receptor substantially in said high affinity state to compete with the agonist-ligand for said both states.

12. The formulation of claim 11, where said second amount is $K_i(K_{DL}K_{DH}/2)^{-1/2}$ the first amount, where $K_{DL}$ and $K_{DH}$ are dissociation constants of said agonist-ligand, and $K_i$ is the dissociation constant of said antagonist-ligand.

13. The formulation of claim 12 wherein an antagonist-/agonist-ligand combination is selected from the group consisting of propranolol/isoproterenol; atenolol/norepinephrine; metoprolol/dobutamine; timolol/ephedrine; 2-amino-5-p phospho-nopentanoic acid/N-methyl-D-aspartic acid; progesterone/oxytocin; sotalol/epinephrine; pindolol/norepinephrine; betaxolol/xamoterol; and propanolol/terbutaline.

14. The formulation of claim 12 further comprising enantiomers of beta-1-antagonists and beta-1-agonists.

15. The formulation of claim 12 wherein an antagonist-/agonist-ligand combination is selected from the group consisting of propranolol/isoproterenol; atenolol/isoproterenol; betaxolol/isoproterenol; metoprolol/isoproterenol; timolol/isoproterenol; sotalol/isoproterenol; pindolol/isoproterenol; betaxolol/isoproterenol; propranolol/epinephrine; atenolol/epinephrine; betaxolol/epincphrine; metoprolol/epinephrine; timolol/epinephrine; sotalol/epincphrine; pindolol/epinephrine; betaxolol/epinephrine; propranolol/terbutaline; atenolol/terbutaline; betaxolol/terbutaline; metoprolol/terbutaline; sotalol/terbutaline; pindolol/terbutaline; betaxolol/terbutaline; propranolol/norepinephrine; atenolol/norepinephrine; betaxolol/norepinephrine; metoprolol/norepinephrine; timolol/norepinephrine; sotalol/norepinephrine; pindolol/norepinephrine; betaxolol/norepinephrine; propranolol/dobutamine; atenolol/dobutamine; betaxolol/dobutamine; metoprolol/dobutamine; timolol/dobutamine; sotalol/dobutamine; pindolol/dobutamine; betaxolol/dobutamine; propranolol/ephedrine; atenolol/ephedrine; betaxolol/ephedrine; metoprolol/ephedrine; timolol/ephedrine; sotalol/ephedrine; pindolol/ephedrine; betaxolol/ephedrine; propranolol/xamoterol; atenolol/xamoterol; betaxolol/xamoterol; metoprolol/xamoterol; timolol/xamoterol; sotalol/xamoterol; pindolol/xamoterol; and betaxolol/xamoterol.

16. The formulation of claim 12 further comprising enantiomers of antagonist: agonist pairings selected from the group consisting of β-1 antagonists: β-2 agonists and β-2 antagonists: β-1 agonists.

* * * * *